US012690796B2

(12) United States Patent
Sunden et al.

(10) Patent No.: US 12,690,796 B2
(45) Date of Patent: Jul. 28, 2026

(54) WEARABLE ECG AND EDA WITH MULTI-LEAD AND SINGLE-LEAD CONNECTIONS

(71) Applicant: Fitbit, Inc., San Francisco, CA (US)

(72) Inventors: Lindsey Michelle Sunden, San Francisco, CA (US); Jens Mitchell Nielsen, San Francisco, CA (US); Anthony Zahi Faranesh, Oakland, CA (US); Man-Chi Liu, San Francisco, CA (US); Jaclyn Leverett Wasson, Alameda, CA (US); Kyung Nim Noh, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 401 days.

(21) Appl. No.: 18/013,599

(22) PCT Filed: Jul. 21, 2021

(86) PCT No.: PCT/US2021/042464
§ 371 (c)(1),
(2) Date: Dec. 29, 2022

(87) PCT Pub. No.: WO2022/020410
PCT Pub. Date: Jan. 27, 2022

(65) Prior Publication Data
US 2023/0240583 A1 Aug. 3, 2023
US 2025/0049372 A9 Feb. 13, 2025

Related U.S. Application Data

(63) Continuation of application No. 16/935,583, filed on Jul. 22, 2020, now abandoned.

(51) Int. Cl.
*A61B 5/318* (2021.01)
*A61B 5/00* (2006.01)
*A61B 5/282* (2021.01)

(52) U.S. Cl.
CPC .............. *A61B 5/318* (2021.01); *A61B 5/282* (2021.01); *A61B 5/681* (2013.01); *A61B 5/6844* (2013.01); *A61B 5/742* (2013.01)

(58) Field of Classification Search
CPC ....... A61B 5/681; A61B 5/053; A61B 5/6843; A61B 2560/0468
See application file for complete search history.

(56) References Cited

U.S. PATENT DOCUMENTS

| | | | |
|---|---|---|---|
| 8,332,019 | B2 | 12/2012 | Shimuta et al. |
| 2004/0204145 | A1 | 10/2004 | Nagatomo |

(Continued)

FOREIGN PATENT DOCUMENTS

| | | |
|---|---|---|
| WO | WO 2019/015294 | 1/2019 |

OTHER PUBLICATIONS

International Preliminary Report on Patentability for Application No. PCT/US2021/042464, mailed Feb. 2, 2023, 8 pages.

(Continued)

*Primary Examiner* — Deborah L Malamud
(74) *Attorney, Agent, or Firm* — DORITY & MANNING P.A.

(57) ABSTRACT

A wellness tracking device includes a plurality of electrodes to receive biometric data from a user. The electrodes may receive an input from the user and transmit information, such as electrical data related to the heart or skin conductance, in order to measurement one or more physical properties. The electrodes may be arranged within the form factor provided by the wellness tracking device and also electrically isolated to provide independent data acquisition for the electrodes. Arrangement of the electrodes may be particularly selected to provide an ergonomic arrangement to enable the user to comfortably provide input data.

15 Claims, 10 Drawing Sheets

(56)     References Cited

U.S. PATENT DOCUMENTS

| | | |
|---|---|---|
| 2018/0014741 A1 | 1/2018 | Chou |
| 2018/0014742 A1 | 1/2018 | Iwawaki |
| 2018/0035910 A1 | 2/2018 | Añó |
| 2018/0049696 A1 | 2/2018 | Eom et al. |
| 2018/0220972 A1 | 8/2018 | Jeong et al. |
| 2018/0235542 A1 | 8/2018 | Yun et al. |
| 2018/0312167 A1 | 11/2018 | Kundu |
| 2019/0059821 A1 | 2/2019 | Pekonen et al. |
| 2019/0274563 A1 | 9/2019 | Soli et al. |
| 2020/0245876 A1 | 8/2020 | Wang et al. |

OTHER PUBLICATIONS

International Search Report for Application No. PCT/ US2021/ 042464, mailed on Oct. 1, 2021, 2 pages.

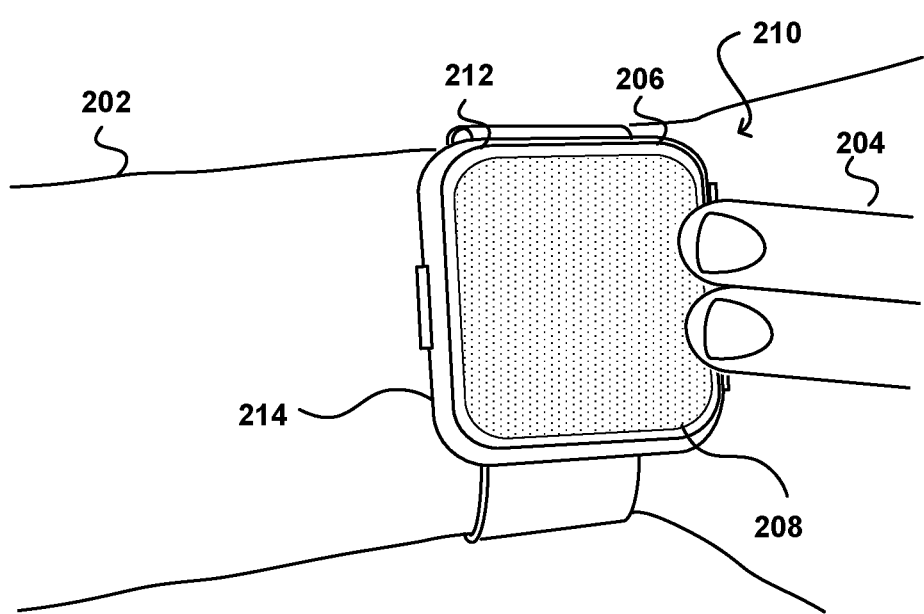
FIG. 2

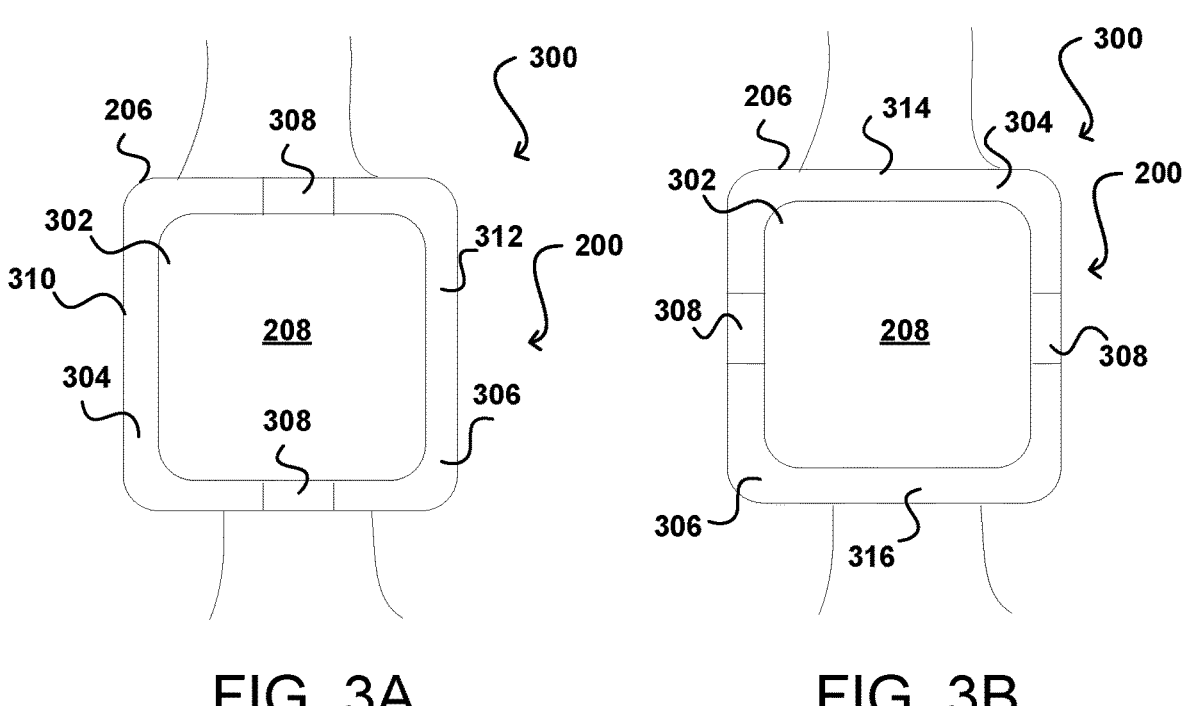
FIG. 3A          FIG. 3B
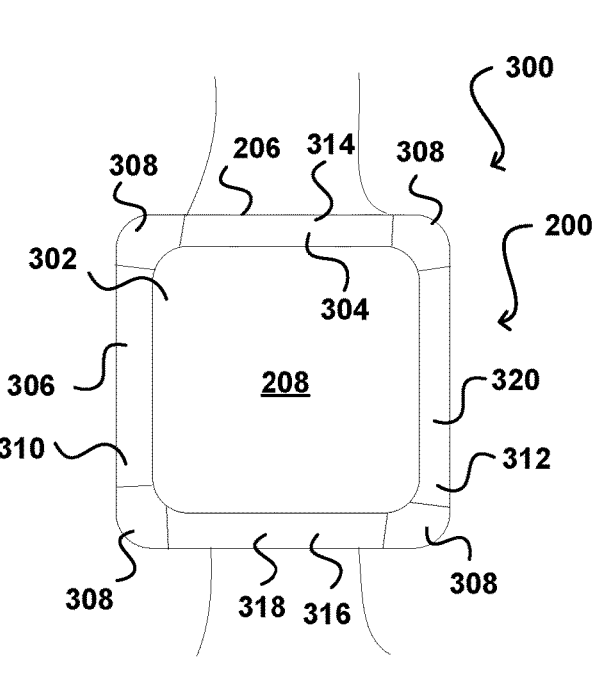
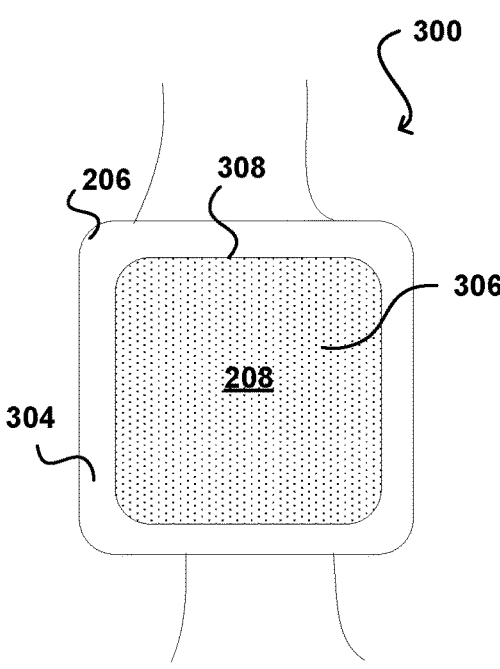
FIG. 3C          FIG. 3D

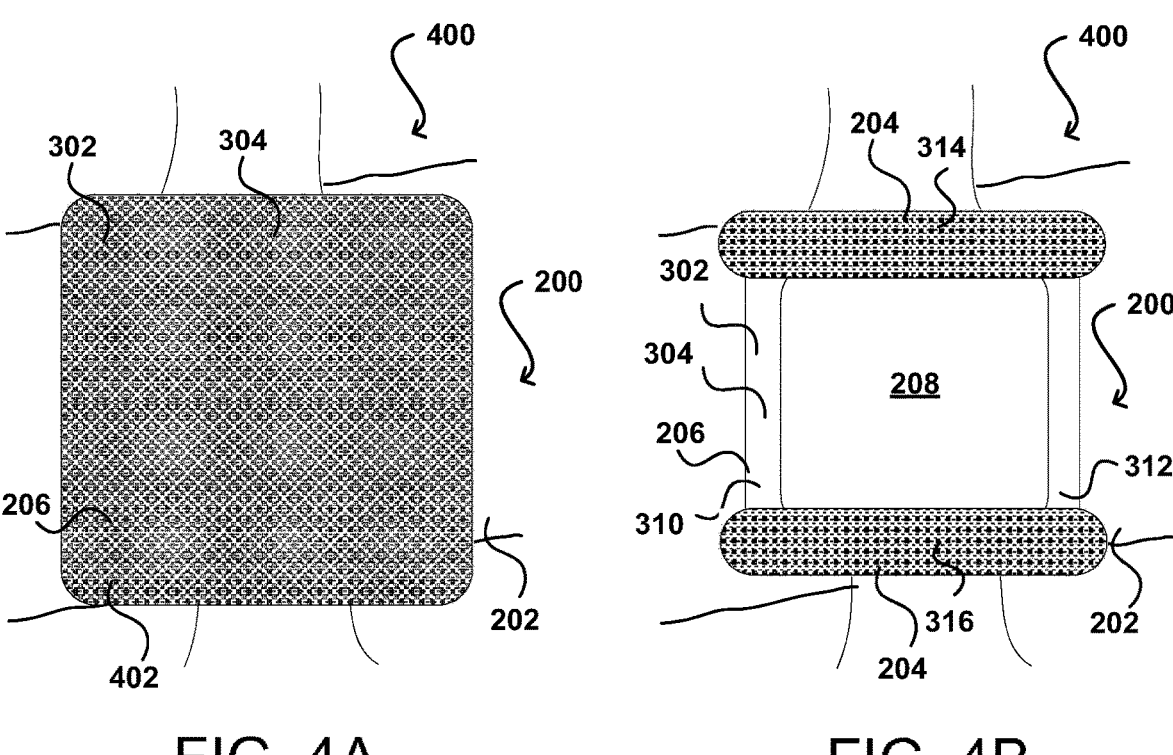
FIG. 4A                    FIG. 4B
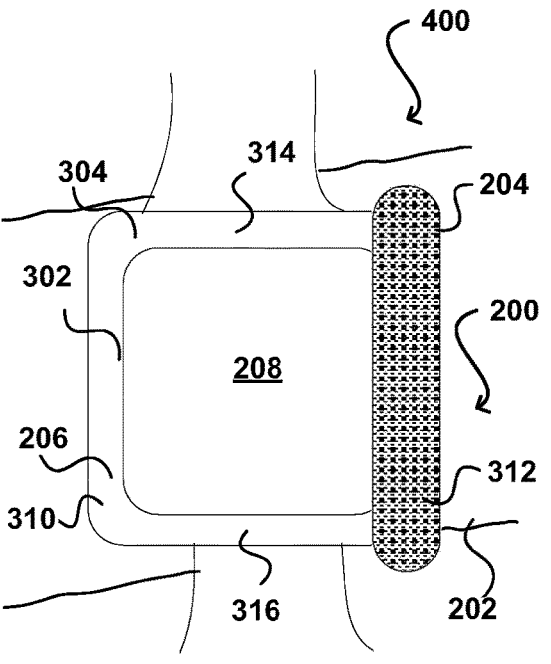
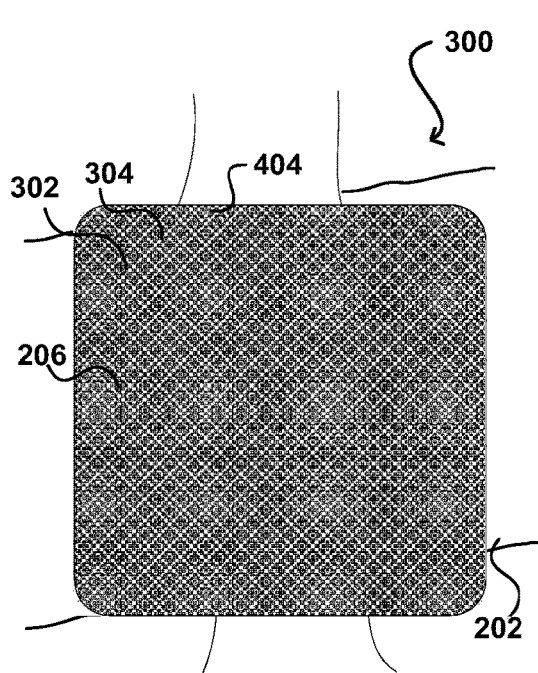
FIG. 4C                    FIG. 4D

500

502

506

504

508

510

512

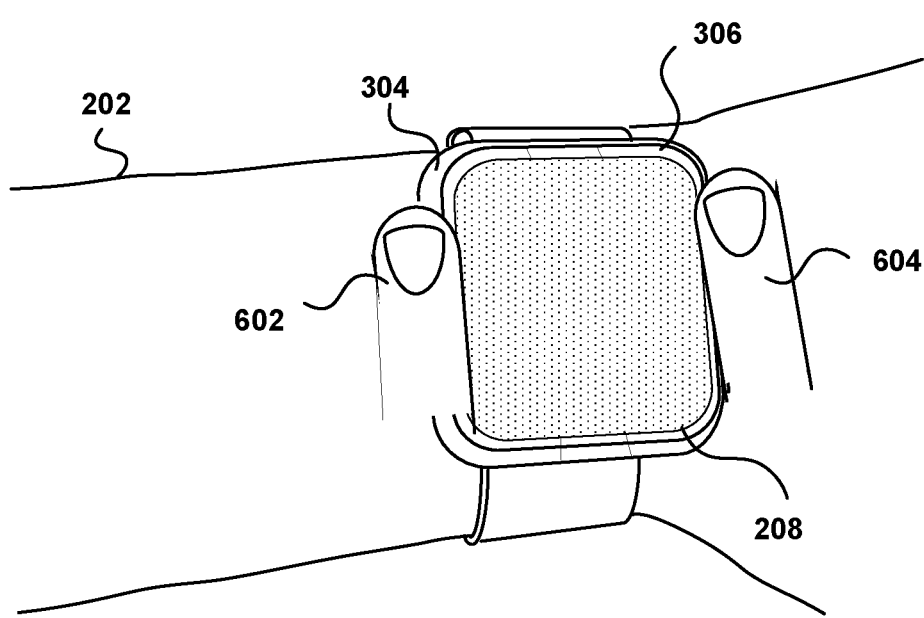
FIG. 6

700

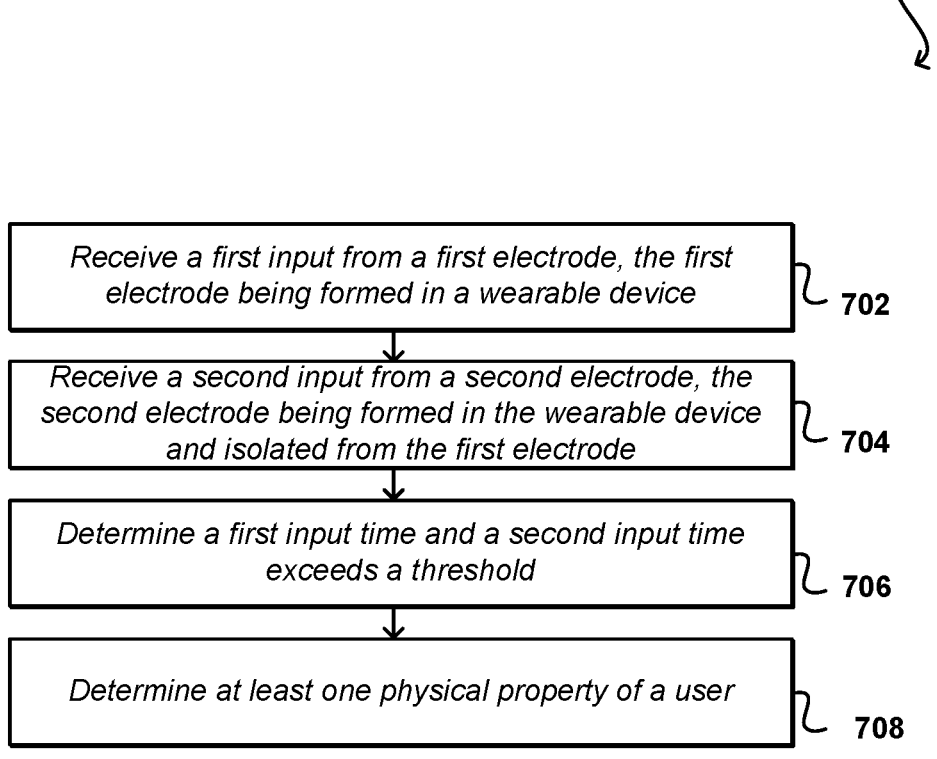

Receive a first input from a first electrode, the first electrode being formed in a wearable device          702

Receive a second input from a second electrode, the second electrode being formed in the wearable device and isolated from the first electrode          704

Determine a first input time and a second input time exceeds a threshold          706

Determine at least one physical property of a user          708

FIG. 7

WEARABLE ECG AND EDA WITH MULTI-LEAD AND SINGLE-LEAD CONNECTIONS

CROSS-REFERENCE TO RELATED APPLICATIONS

The present application is based upon and claims the right of priority under 35 U.S.C. § 371 to International Application No. PCT/US2021/042464 filed on Jul. 21, 2021, which claims priority to U.S. patent application Ser. No. 16/935,583, filed on Jul. 22, 2020, each of which are incorporated by reference herein in their entirety for all purposes.

BACKGROUND

Wearable electronic devices have gained popularity among consumers. A wearable electronic device may track a user's activities or biometric data using a variety of sensors. Data captured from these sensors can be analyzed in order to provide a user with information, such as an estimation of how far they walked in a day, their heart rate, how much time they spent sleeping, and the like. However, it may be challenging for users to comfortably obtain each measurement using the wearable device, and as a result, the user may not fully utilize the capabilities of the device.

BRIEF DESCRIPTION OF THE DRAWINGS

Various embodiments in accordance with the present disclosure will be described with reference to the drawings, in which:

FIG. 2 illustrates an example of a user interacting with a wearable device on an extremity, in accordance with embodiments of the present disclosure.

FIGS. 3A-3D illustrate schematic top plan views of embodiments of electrode configurations of a wearable device, in accordance with various embodiments of the present disclosure.

FIGS. 4A-4F illustrate schematic top plan views of embodiments of user interactions with a wearable device, in accordance with embodiments of the present disclosure.

FIG. 6 illustrates an example of a user interacting with a wearable device on an extremity, in accordance with embodiments of the present disclosure.

FIG. 7 illustrates an example process for collecting data from a wearable device, in accordance with embodiments of the present disclosure.

DETAILED DESCRIPTION

Figure 1:
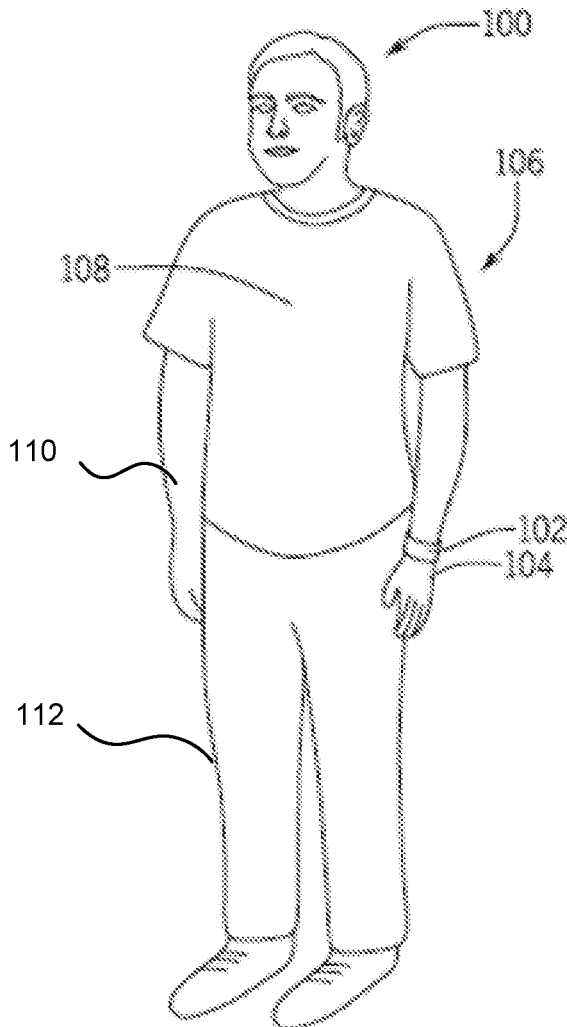
FIG. 1 illustrates an example of a user with a wearable device on an extremity, in accordance with various embodiments of the present disclosure.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods in accordance with various embodiments of the present disclosure may overcome one or more of the aforementioned and other deficiencies experienced in conventional approaches for wearable devices, such as electronic wellness trackers. For example, in various embodiments, capabilities may be integrated into the wearable device to enable electrocardiogram (ECG) and/or electrodermal activity (EDA). The wearable device may utilize either a single-lead or a multi-lead approach to obtaining the information for ECG and/or EDA. The single-lead and/or multi-lead may refer to a number of leads arranged on a face of the wearable device.

Typically, ECG measurements require conductive contacts taken across a body (e.g., across the heart) in order to measure electrical activity of the heart. As a result, typically two different devices and/or sensor arrangements are utilized, which may be uncomfortable for a user to wear continuously. Additionally, trying to incorporate the capabilities into the form factor of a wearable device, such as a watch or fitness tracker, may be challenging due to the small footprint and also shielding requirements in order to include two separate leads. Moreover, relative sizes of the leads may affect the quality of signal received. Embodiments of the present disclosure include functionality for ECG measurements incorporated into the form factor of a wearable device, such as a watch. A first contact may be arranged on a bottom portion of the wearable device, which may be the portion in direct and/or continuous contact with a user's extremity, such as a wrist. In other words, the first contact may be arranged on the portion of the wearable device facing the wrist or body of the user. The second contact may be arranged along a face or bezel of the wearable, which may be proximate a top portion of the wearable device (e.g., opposite the first contact). Such an arrangement may enable the user to comfortability obtain the ECG measurements, for example, by placing an extremity opposite a wearing location of the wearable device along the top of the wearable device.

Embodiments of the present disclosure may include a single lead or multiple leads for obtaining the ECG and/or EDA measurements. For example, a single lead may be incorporated into a bezel and/or screen of the wearable device. Additionally, in embodiments, multiple leads may also be incorporated into the bezel and/or screen. For example, different regions of the bezel may include different leads, which may be isolated from adjacent leads. Additionally, plated electrodes and the like may be incorporated into various components of the wearable device in order to provide conductive contacts that may act as leads for obtaining various measurements.

In various embodiments, EDA measurements may be obtained using a user's fingers, which may provide more accurate information than, for example, a user's arms or chest. In various embodiments, a single lead or multi-lead portion of the wearable device may provide a region where the user may position their fingers (or other body parts), measure a skin conductance, and determine a value associated with a user's stress level associated with the sympathetic nervous system. As noted above, the leads may be arranged to provide a comfortable, ergonomic position for the user. Accordingly, if the user is comfortable during the measurement or the measurement is not onerous for the user, the user is more likely to utilize the functionality of the wearable device.

FIG. 1 illustrates an example of a user 100 wearing a user monitoring device 102 around a wrist 104 of the user 100. The user monitoring device 102 may also be referred to as a wearable or a fitness tracker, and may also include devices that are worn around the chest, legs, head, or other body part, or a device to be clipped or otherwise attached onto an article of clothing worn by the user 100. The user monitoring device 102 may collectively or respectively capture data related to any one or more of caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, respiration rate and patterns, various body movements, among others. Additional data may be provided from an external source, e.g., the user may input their height, weight, age, stride, or other data in a user profile on a fitness-tracking website or application and such information may be used in combination with some of the above-described data to make certain evaluation or in determining user behaviors, such as the distance traveled or calories burned of the user. The user monitoring devices may also measure or calculate metrics related to the environment around the user such as barometric pressure, weather conditions, light exposure, noise exposure, and magnetic field.

In some embodiments, the user monitoring device 102 may be connected to a network directly, or via an intermediary device. For example, the user monitoring device 102 may be connected to the intermediary device via a BLU-ETOOTH® connection, and the intermediary device may be connected to the network via an Internet connection. In various embodiments, a user may be associated with a user account, and the user account may be associated with (i.e., signed onto) a plurality of different networked devices. In some embodiments, additional devices may provide any of the abovementioned data among other data, and/or receive the data for various processing or analysis. The additional devices may include a computer, a server, a handheld device, a temperature regulation device, or a vehicle, among others.

In the illustrated embodiment, the user monitoring device 102 may include a conductive bottom plate that is positioned against a wrist of the user 100, in the illustrated embodiment where the user monitoring device 102 is worn on the wrist. This conductive bottom plate may serve as a first lead (e.g., first electrode) for obtaining various measurement data, such as for ECG. Additionally, in embodiments, one or more additional conductive areas (e.g., leads, electrodes) may be integrated into other areas of the user monitoring device 102. A location of the various additional leads may be particularly selected to enable certain types of measurements (e.g., ECG, EDA, etc.) and/or provide an ergonomic position for the user 100 while the data is collected. For example, it would be uncomfortable for the user to place a bottom of their foot on the user monitoring device 102. However, placing their opposite hand along a top of the user monitoring device 102 may be easy, and as a result, the user 100 may be more likely to utilize the features of the user monitoring device 102.

FIG. 1 illustrates the user monitoring device 102 positioned on the wrist 104 of an extremity 106 of the user, which is the user's left arm. During normal operation, the user 100 may swing their arm 106 while walking, or change position of their arm 106 for a variety of reasons, and as a result it may be difficult to obtain various measurements, such as ECG or EDA, without incorporating additional sensors or instructions of the user to follow. For example, ECG measurements evaluate electrical activity across the heart 108, and as a result, an opposite extremity 110, 112 is utilized to obtain the measurement. However, the user may not be comfortable wearing two wearable devices, such as a second watch or a wrist cuff, and therefore, may not utilize the full functionality of the user monitoring device 102. Moreover, healthcare professionals may be frustrated that the user is unwilling to acquire the data necessary to diagnose or treat illnesses. Embodiments of the present disclosure are directed toward integration of various measurements in the user monitoring device 102, for example through incorporation of one or more leads into the user monitoring device 102.

FIG. 2 illustrates an example wearable device 200 that can be utilized in accordance with various embodiments. In this example the device is a smart watch, although fitness trackers and other types of devices can be utilized as well. Further, although this device is shown to be worn on a user's wrist, similar to the example of FIG. 1, there can be other types of devices worn on, or proximate to, other portions of a user's body as well, such as on a finger, in an ear, around a chest, etc. For many of these devices there will be at least some amount of wireless connectivity, enabling data transfer between a networked device or computing device and the wearable device. This might take the form of a BLU-ETOOTH® connection enabling specified data to be synchronized between a user computing device and the wearable device, or a cellular or Wi-Fi connection enabling data to be transmitted across at least one network such as the Internet or a cellular network, among other such options.

As mentioned, there can be various other types of functionality offered by such a wearable device, as may relate to the health of a person wearing the device. One such type of functionality relates to ECG. ECG is a process that can be used to determine and/or track the activity of the heart of a person over a period of time. In order to obtain ECG data, a conductive electrode is often brought into contact with the skin of the person to be monitored. In the example situation of FIG. 2, a person is wearing a wearable device 200 on his or her arm 202, and can bring one or more fingers 204 (or palm, etc.) into contact with an exposed electrode of the device. In this example, the electrode is at least a portion of a conductive ring 206 that is part of the housing around a display screen 208 of the wearable device, although other types and forms of electrodes can be used as well within the scope of the various embodiments. In embodiments, this housing may also be referred to as a bezel that forms an outline around the display screen 208. The electrode can be connected to an ECG circuit that can detect small changes in electrical charge on the skin that vary with the user's heartbeat. ECG data can be monitored over time to attempt to determine irregularities in heartbeat that might indicate serious cardiac issues. Conventional ECG measurements are obtained by measuring the electrical potential of the heart over a period of time, typically corresponding to multiple cardiac cycles. By a user placing his or her fingers on the exposed electrode for a minimum period of time, during which ECG measurements are taken, an application executing on the wearable device can collect and analyze the ECG data and provide feedback to the user.

As mentioned, ECG measurements are taken across opposite extremities. For example, with reference to FIG. 2, a first point is along the arm 202 (e.g., via a conductor on the underside of the wearable device 200), and a second point at the fingers 204 of the opposite arm contacting the conductor ring 206. As a result, the signal evaluates a circuit including the heart. Because the ECG is incorporated in the wearable device 200, both electrodes that form a single lead ECG sensor are incorporated into the simple device, unlike traditional methods that may utilize two or more separate sensors. In various embodiments, the electrodes are electrically isolated from the device to facilitate appropriate functionality.

A user's skin impedance may decrease the reliability of data captured for the ECG measurement. As a result, reducing skin impedance is desirable. Accordingly, increasing contact surface area for each electrode is desirable. For example, forming substantially all of the bottom face of the wearable device 200 may increase the surface area in contact with the arm 202, while increasing a size of the conductive ring 206 may also decrease skin impedance. Moreover, as noted above, in various embodiments the second electrode may include one or more plated electrodes or other conductive elements that are integrated into the display screen 208, thereby increasing the conductive surface area for the second electrode.

The illustrated wearable device includes a housing 210. The housing 210 may be a multi-part component, such that the housing 210 is split into a first part 212 and a second part 214. However, it should be appreciate that there may be additional parts. Moreover, in embodiments, additional components may be utilized to form one or more parts. For example, the conductive ring 206 may form a portion of a bezel of the first part 212. The housing 210 may enclose one or more electronic components, which may be utilized to collect and/or analyze data, as described herein. For example, the housing 210 may enclose appropriate circuitry for ECG and/or EDA measurements.

In various embodiments, ergonomics and user comfort are emphasized in order to decrease the likelihood of user error and/or encourage users to utilize the functionality of the wearable device 200. For example, increasing the surface area of the electrodes may prevent shorts across both electrodes because it will be easier for the user to identify a region associated with one of the two electrodes.

Additionally, to further prevent user error during electrical measurements, locations for the electrodes may be particularly selected to provide comfort for users to maintain a stationary pose. For example, measurement data may be acquired over a period of time, such as 60 seconds, or longer. Movement may disrupt the measurements, and therefore, the location of the electrodes may be selected such that the user can maintain position to acquire the data. The particularly selected locations may be selected with user comfort in mind, as well as providing flexibility to enable the user to interact with the wearable device in a variety of ways. For example, different users may have ailments that make interaction with the devices difficult (e.g., arthritis, carpal tunnel, amputations, etc.), so providing a wide variety of potential interaction methods provides a greater range of use over a wider group of users.

As noted above, embodiments of the present disclosure may include a system that includes at least 2 independent electrodes, electrically isolated within a single device. For example, a first electrode may utilize a bottom surface area of the wearable device 200 (not pictured in FIG. 2). The bottom surface area, or a portion thereof, may make contact with the wrist 202. As will be appreciated, the bottom surface area may have one of the largest continuous surface areas for the wearable device 200, thereby achieving a goal described above to increase surface area and reduce skin impedance. In various embodiments, the first electrode is formed from a conductive electrode material and may be electrically isolated from the remainder of the device, for example by incorporating insulating material into the wearable device 200, such as plastics and the like. A second electrode may utilize a top surface area, or a portion thereof, of the wearable device 200. This area may be positioned such that a user can easily access the area and intuitively interact with the area. In a variety of embodiments, wearable devices may include the display screens 208 that occupy a large portion of the top surface area, as users may prefer large displays. Accordingly, the second electrode may be incorporated into the bezel surrounding the display screen 208, as illustrated by the conductive ring 206. However, it should be appreciated that, in various embodiments, at least a portion of the display screen 208 may be utilized as the second electrode using methods that would not occlude the display, for example, by coating the display screen 208 in a conductive material (e.g., indium tin oxide), local extension of the sensor to not occlude the display, and the like. Moreover, in various embodiments, the screen 208 may be omitted from the wearable device 200. As a result, the top surface could be substantially identical to the bottom surface. It should be appreciated that the second electrode may further be comprised of two separate, electrically isolated electrodes. For example, in various embodiments, a portion of the metallic ring 206 may be segmented and isolated from a different portion of the ring.

As noted above, embodiments of the present disclosure may go beyond configurations that include a single top electrode and a single bottom electrode to include multiple leads along the wearable device (e.g., more than one lead on the top, more than one lead on the bottom, more than one lead on both the top and bottom). Adding an electrode to the top of the wearable device 200, as described below, increases the number of ECGs and provides additional wearer configurations for obtaining measurement information. By way of example, configurations that include two electrodes along the top of the wearable device enable multiple different positions to obtain information, such as right arm to left leg and left arm to left leg, as well as augmented limb leads (e.g., aVR, aVL, and aVF). These additional leads may enable screening of a broader range of non-rhythm based conditions, and could ergonomically work by users holding the top of the device with two thumbs and pressing the bottom of the device into their leg, as an example.

While single-lead ECG can provide accurate information with regards to beat timing (also called RR interval), which can be sufficient for diagnosing many arrhythmias, multiple leads can provide additional information to more accurately diagnose conditions which rely on ECG morphology (shape). For example, sinus tachycardia is a regular rhythm that is faster than normal, and can be diagnosed from a single lead. Several conditions can cause a deviation of the electrical axis or an abnormal R-wave amplitude, which is best observed using multiple leads. Embodiments described herein may also use multi-lead ECG to examine other morphologies, such as ST-elevation or depression. Moreover, as noted above, including at least two sensors on the top may also enable EDA measurements.

As described, embodiments of the present disclosure enable multiple different user configurations for obtaining measurements using two or more leads, such as for ECG or EDA. EDA is a measurement of skin electrical resistance or conductance, which reflects the sympathetic activation in the secretory activity of sweat glands. It has been used in psychological research to understand autonomic nervous system activity and identify acute stress events induced by physical, mental, or cognitive stimuli. The skin conductance/resistance can be measured by injecting a small current between two electrodes in contact with the skin. In many instances, EDA is measured at the fingers, palm, or feet. However, in certain embodiments, wrist measurements may also be utilized for EDA. Utilizing configurations having two electrodes at the top surface of the wearable device, EDA measurements may be obtained from users in a simple, compact, and comfortable form factor.

FIGS. 3A-3D are schematic top plan views of examples 300 of a top surface 302 of the wearable device 200. In the illustrated embodiments, the top surface 302 includes the conductive ring 206 and the display screen 208. As noted above, the conductive ring 206 may form at least a portion of a bezel surrounding the display screen 208 and, in various embodiments, may be segmented into different portions to include one or more electrodes. The example 300 of FIG. 3A illustrates a multi-electrode configuration where the conductive ring 206 includes a first electrode 304 and a second electrode 306. The illustrated first and second electrodes 304, 306 are isolated from one another by a spacer 308, which may be any electrically isolating, non-conductive material, such as a plastic. As a result, a user may engage the first and second electrodes 304, 306 separately in order to obtain a variety of different measurements. For example, in the configuration shown in FIG. 3A with the first and second electrodes 304, 306, the user could place a finger from their left hand on the first electrode 304 and a finger from their right hand on the second electrode 306 to obtain an ECG measurement because the circuit would be completed while traveling across the chest of the user. Additional configurations are also possible and are described in more detail herein.

FIG. 3B illustrates the first and second electrodes 304, 306 arranged on different portions of the conductive ring 206. For example, when compared to the configuration of FIG. 3A, which has the first and second electrodes 304, 306 along the sides 310, 312, the illustrated embodiment includes the first and second electrodes 304, 306 along the top and bottom 314, 316. It should be appreciated that these locations are for illustrative purposes only, and that the electrodes could also be placed at the corners, or any other location around the conductive ring 206. Additionally, while FIGS. 3A and 3B illustrate substantially symmetrical conductive rings 206, it should be appreciated that the electrodes 304, 306 may be arranged at any desirable location and are not necessarily symmetrical. Moreover, the electrodes 304, 306 may not be the same size.

The example 300 of FIG. 3C includes four different electrodes positioned along the conductive ring 206. It should be appreciated that including four electrodes is for illustrative purposes only, and that there may be three, five, six, or any reasonable number of electrodes. In the illustrated embodiment, the first electrode 304 is arranged along the top 314, the second electrode 306 is arranged along the side 310, a third electrode 318 is arranged along the bottom 316, and a fourth electrode 320 is arranged along the side 312. Each electrode is isolated from the adjacent ones by respective spacers 308, which as noted above are formed from non-conductive, isolating material. Accordingly, in various embodiments, different numbers of electrodes in a variety of configurations may be utilized.

In the embodiment illustrated in FIG. 3D, the wearable device 200 includes the conductive ring 206 that includes the first electrode 304. In other words, the first electrode 304 is a substantially continuous electrode formed within the conductive ring 206. Additionally, as noted above, the display screen 208 includes the second electrode 306 in the form of a conductive film or coating. In various embodiments, the spacer 308 is positioned between the bezel and the display screen 208 in order to electrically isolate the electrodes from one another. However, it should be appreciated that in embodiments where the conductive ring 206 acts as a single electrode that the display screen 208 may not be an electrode. Similarly, in embodiments where the display screen 208 is an electrode, the bezel may not be an electrode.

It should be appreciated that while various embodiments may describe the electrodes as being incorporated into the bezel, that the conductive portions may also be a coating or film, as noted above. For example, a portion of the screen 208 may be coated by an electrically conductive material and utilized as an electrode. Additionally, other isolating materials may further be incorporated in order to enable any reasonable number of different electrodes on the top surface 302. It should be appreciated that the form fact of the wearable device 200, among other factors, may at least partially guide final locations for the electrodes, as it is desirable to position the electrodes in a way that a user will be comfortable using the wearable device 200. Additionally, sizes of the electrodes and spacers may be particularly selected, based at least in part on relative sizes of the wearable device 200.

FIGS. 4A-4F are schematic top plan views of examples 400 of user body configurations that may be utilized to obtain measurements from the wearable device, such as ECG or EDA measurements. In the illustrated embodiment, the conductive ring 206 is positioned about the display screen 208. It should be appreciated that the conductive ring 206 may include one or more electrodes, such as the configurations illustrated in FIGS. 3A-3D. Moreover, the display screen 208 may also include an electrode, as noted in FIG. 3D. For ease with the following discussion, the conductive ring 206 will be described as including a single electrode, but such discussion is not intended to limit the scope of the present disclosure, and it should be appreciated that similar configurations may also be utilized with the embodiments having two or more electrodes integrated into the top surface 302 of the wearable device 200.

The example 400 of FIG. 4A includes the wearable device 200 arranged along the arm 202 of the user. The arm 202 will be described as the left arm for ease of explanation, but the right arm is also applicable. Moreover, the arm 202 is used as an example and the wearable device 200 may be positioned along an ankle or other extremity of the user. The top surface 302 includes the conductive ring 206, which may be referred to as the first electrode 304. The second electrode 306 in the illustrated embodiment is on a bottom surface of the wearable device 200 and is in contact with the arm 202. Thereafter, the user can obtain measurement information, such as for ECG, by positioning a palm or wrist 402 of their opposite arm (e.g., right in the illustrated embodiment) over the top surface 302 to engage the first electrode 304. The illustrated embodiment includes the palm 402 having a patterned, semi-transparent configuration in order to show the top surface 302 below the palm 402. As noted above, the configuration of FIG. 4A may be comfortable for users because of the large surface area made available for contact by the conductive ring 206. The user may simply place their hand over the device, which is less intrusive than other methods. Additionally, because movement may be detrimental to obtaining measurements, the illustrated configuration is ergonomically comfortable for the user, and as a result, the user may maintain this position for a period of time (e.g., a predetermined period of time) to enable data collection.

The example 400 of FIG. 4B includes the wearable device 200 arranged along the arm 202 of the user (left arm in this example). The top surface 302 includes the conductive ring 206, which may be referred to as the first electrode 304. The second electrode 306 in the illustrated embodiment is on a bottom surface of the wearable device 200 and is in contact with the arm 202. Thereafter, the user can obtain measurement information, such as for ECG or EDA, by positioning two fingers 204 along the conductive ring 206. This configuration may be described as a "U" or "pinch" grip. It should be appreciated that the fingers 204 may be arranged along the sides 310, 312 in other embodiments, and that the positioning along the top 314 and bottom 316 is for illustrative purposes only. The illustrated embodiment includes the fingers 204 having a patterned, semi-transparent configuration in order to show the top surface 302 below the fingers 204. As noted above, the configuration of FIG. 4B may be comfortable for users because of the large surface area made available for contact by the conductive ring 206. The user may simply place their hand over the device and align their fingers with the conductive ring 206, which is less intrusive than other methods. Additionally, due to concerns with movement noted herein, the illustrated configuration is ergonomically comfortable for the user because it provides options for how the user positions their fingers along the conductive ring, and as a result, the user may maintain this position for a period of time (e.g., a predetermined period of time) to enable data collection.

The example 400 of FIG. 4C includes the wearable device 200 arranged along the arm 202 of the user (left arm in this example). The top surface 302 includes the conductive ring 206, which may be referred to as the first electrode 304. The second electrode 306 in the illustrated embodiment is on a bottom surface of the wearable device 200 and is in contact with the arm 202. Thereafter, the user can obtain measurement information, such as for ECG or EDA, by positioning a finger 204 along the conductive ring 206. It should be appreciated that the finger 204 positioned along the side 312 is for illustrative purposes only and that, in other embodiments, the finger 204 may be arranged along the side 310, the top 314, and/or the bottom 316. The illustrated embodiment includes the finger 204 having a patterned, semi-transparent configuration in order to show the top surface 302 below the finger 204. As noted above, the configuration of FIG. 4C may be comfortable for users because of the large surface area made available for contact by the conductive ring 206. The user may simply place their hand over the device and align their finger with the conductive ring 206, which is less intrusive than other methods. Additionally, due to concerns with movement noted herein, the illustrated configuration is ergonomically comfortable for the user because it provides options for how the user positions their fingers along the conductive ring, and as a result, the user may maintain this position for a period of time (e.g., a predetermined period of time) to enable data collection.

The example 400 of FIG. 4D includes the wearable device 200 arranged along the arm 202 of the user (left arm in this example). The top surface 302 includes the conductive ring 206, which may be referred to as the first electrode 304. The second electrode 306 in the illustrated embodiment is on a bottom surface of the wearable device 200 and is in contact with the arm 202. Thereafter, the user can obtain measurement information, such as for ECG or EDA, by positioning a leg 404 along the conductive ring 206. For example, in the illustrated embodiment the user may bring their right leg up and place it over the conductive ring 206. Such an arrangement would provide a measurement across the chest and also enhance comfort, because the user may sit cross-legged with the wearable device 200 under their leg. The illustrated embodiment includes the leg 404 having a patterned, semi-transparent configuration in order to show the top surface 302 below the leg 404. As noted above, the configuration of FIG. 4D may be comfortable for users because of the large surface area made available for contact by the conductive ring 206. The user may simply place their leg over the device, for example while sitting, which is less intrusive than other methods. Additionally, due to concerns with movement noted herein, the illustrated configuration is ergonomically comfortable for the user because it provides options for how the user positions their leg along the conductive ring, and as a result, the user may maintain this position for a period of time (e.g., a predetermined period of time) to enable data collection.

Figure 4E:
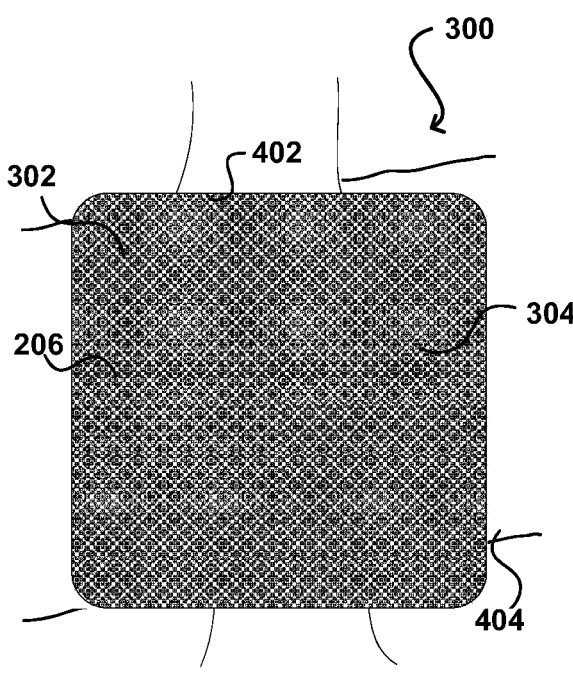

The example 400 of FIG. 4E includes the wearable device 200 arranged along the leg 404 of the user (left leg in this example). The top surface 302 includes the conductive ring 206, which may be referred to as the first electrode 304. The second electrode 306 in the illustrated embodiment is on a bottom surface of the wearable device 200 and is in contact with the leg 404. Thereafter, the user can obtain measurement information, such as for ECG or EDA, by positioning the palm 402 along the conductive ring 206. For example, in the illustrated embodiment the user may bring their right arm toward the conductive ring 206 and position their hand over the conductive ring 206. Such an arrangement would provide a measurement across the chest and also enhance comfort, because the user may sit cross-legged with the wearable device 200 under their hand. The illustrated embodiment includes the palm 402 having a patterned, semi-transparent configuration in order to show the top surface 302 below the palm 402. As noted above, the configuration of FIG. 4E may be comfortable for users because of the large surface area made available for contact by the conductive ring 206. The user may simply place their hand over the device while comfortably sitting. Additionally, due to concerns with movement noted herein, the illustrated configuration is ergonomically comfortable for the user because it provides options for how the user positions their leg and then contacts the conductive ring with an opposite hand, and as a result, the user may maintain this position for a period of time (e.g., a predetermined period of time) to enable data collection.

Figure 4F:
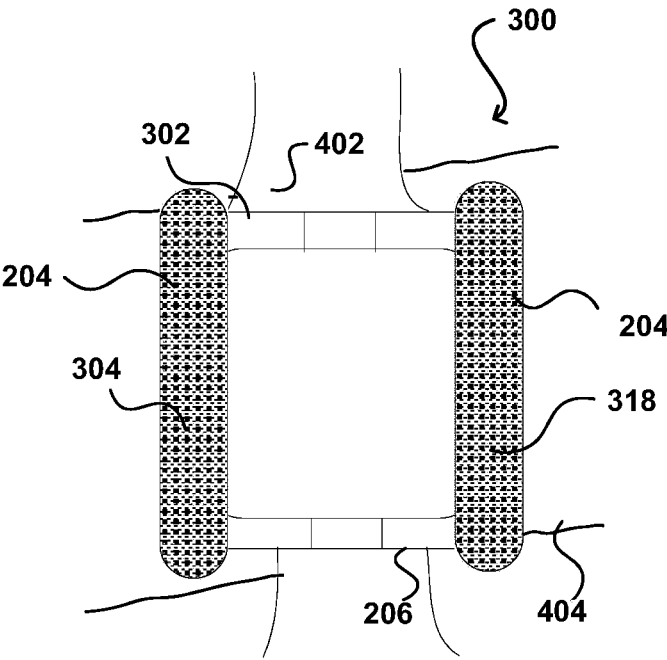

The example 400 of FIG. 4F includes the wearable device 200 arranged along the leg 404 of the user (left leg in this example). The top surface 302 includes the conductive ring 206, which may be referred to as the first electrode 304. The second electrode 306 in the illustrated embodiment is on a bottom surface of the wearable device 200 and is in contact with the leg 404. Further illustrated in the embodiment of FIG. 4F is the third electrode 318, also arranged along the top surface 302. As noted above, the third electrode 318 may be electrically isolated from the first electrode 304 and the second electrode 306. Thereafter, the user can obtain measurement information, such as for ECG or EDA, by positioning the fingers 204 along the first and third electrodes 304, 318 and holding the second electrode 306 against the leg 404. In this manner, the user may utilize the functionality of the device without actually wearing the device, as the user may retrieve the wearable device and take the measurement without securing the wearable device to an extremity. This may be advantageous for users that do not want to wear the device, but want to receive the benefits the measurements provide. Additionally, the configuration is still comfortable for users, and as a result, the user may maintain this position for a period of time (e.g., a predetermined period of time) to enable data collection.

Figure 5:
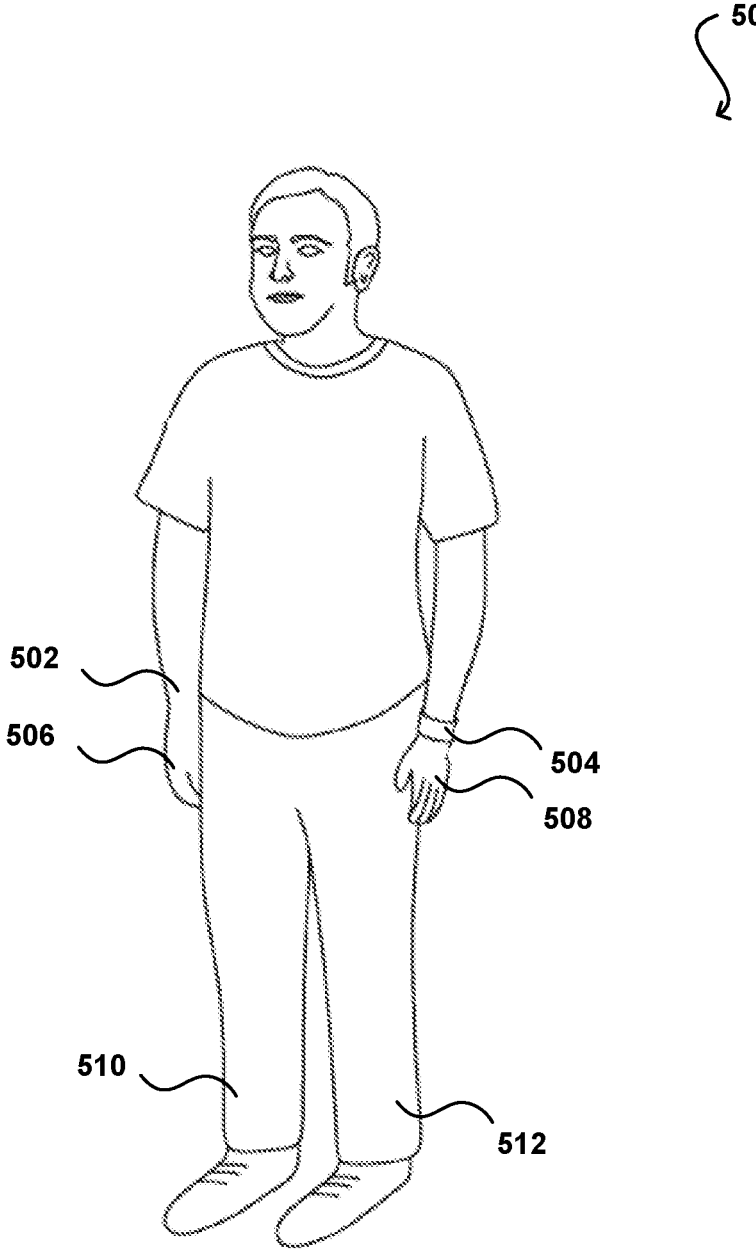
FIG. 5 illustrates an example user with a wearable device on an extremity, in accordance with various embodiments of the present disclosure.

FIG. 5 is a schematic diagram of a person 500 illustrating potential locations for obtaining measurement data using the wearable device. In various embodiments, the wearable device includes two electrodes along the top surface and one along the bottom surface, however, it should be appreciated that there may be more or fewer electrodes on both the top and bottom surfaces. In the illustrated embodiment, potential contacts points are generalized such that a location at the wrist is reflective of the arm, a location at the hand is reflective of the palms and/or fingers, and a location at the leg is reflective of the entire leg. In the illustrated embodiment, the location 502 corresponds to the right arm, the location 504 corresponds to the left arm, the location 506 corresponds to the right hand, the location 508 corresponds to the left hand, the location 510 corresponds to the right leg, and the location 512 corresponds to the left leg.

In various embodiments, different cross body measurements may be acquired utilizing one or more of the locations and the wearable device. For example, the table below illustrates potential cross body measurement configurations. It should be appreciated that this table is a non-limiting example and that other configurations may be utilized. Moreover, contact may be made as illustrated in FIGS. 4A-4E, among other options, such that a contact between the right arm and the left hand may include the palm of the left hand, the fingers of the left hand, or the other potential configurations.

| Wearable Device Location/Contact | Cross-Body Contact |
| --- | --- |
| Right Arm (502) | Left Arm (504) |
| Right Arm (502) | Left Hand (508) |
| Right Arm (502) | Left Leg (512) |
| Left Arm (504) | Right Arm (502) |
| Left Arm (504) | Right Hand (506) |
| Left Arm (504) | Right Leg (510) |
| Right Hand (502) | Left Arm (504) |
| Right Hand (502) | Left Hand (508) |
| Right Hand (502) | Left Leg (512) |
| Left Hand (508) | Right Arm (502) |
| Left Hand (508) | Right Hand (506) |
| Left Hand (508) | Right Leg (510) |
| Right Leg (510) | Left Arm (504) |
| Right Leg (510) | Left Hand (508) |
| Right Leg (510) | Left Leg (512) |
| Left Leg (512) | Right Arm (502) |
| Left Leg (512) | Right Hand (506) |
| Left Leg (512) | Right Leg (510) |

It should be appreciated that the example is for illustrative purposes only and that the wearable device could also be positioned at other locations, such as the neck, nears, face, scalp, and various others. Furthermore, embodiments that utilize additional electrodes similarly have additional potential configurations, as noted above.

FIG. 6 is a schematic top view of an example 600 EDA data acquisition event in which the wearable device 200 is arranged along the arm 202. The illustrated wearable device 200 includes the first electrode 304 and the second electrode 306, separated by the spacers 308. In operation, the user brings a first finger 602 into contact with the first electrode 304 and a second finger 604 into contact with the second electrode 306. A current is introduced between the first electrode and the second electrode 306 in order to measure the conductance of the skin. As a result, measurements related to EDA for the user may be obtained using the wearable device 200. For example, a magnitude of electrical conductance may be greater when a person is sweating, indicating some type of stress level. In various embodiments, the display 208 may include instructions for the user to follow, such as describing where to locate the fingers 602, 604 and/or how long to keep the fingers 602, 604 in position, among other instructions. The inclusion of the multi-electrode top surface enables the EDA to be incorporated into the form factor provided by the wearable device, while still enabling comfortable. As a result, additional information may be obtained by the user in order to ascertain stress levels. In various embodiments, elevated stress levels may be monitored and pair with applications from a provider, such as breathing exercises or mediation exercises in order to reduce stress levels.

It should be appreciated that while the illustrated embodiment describes using the fingers 602, 604, in various embodiments the bottom side of the wearable device may be utilized to obtain EDA measurements from the arm of the user. For example, in embodiments, the bottom side may include two or more electrodes.

FIG. 7 is a flow chart of an example process 700 for obtaining physical measurements from a user of a wearable device. It should be understood that, for any process discussed herein, there can be additional, fewer, or alternative steps performed in similar or alternative orders, or in parallel, within the scope of the various embodiments. In this example, a first input is received from a first electrode (702). The first electrode may be formed in a wearable device and the input may be a result of engagement with the first electrode by a user. As described, the user may contact the first electrode with an extremity, such as their wrist, leg, hand, or the like. In various embodiments, contact with the first electrode for a sufficient period of time may be considered sufficient to generate the input. For example, momentary, accidental contact may not provide enough information to be considered an input, while a longer, intentional contact may be sufficient.

The method also includes receiving a second input, from a second electrode (704). In various embodiments, the second electrode is different from and electrically isolated from the first electrode. For example, as noted above, an electrically insulated spacer may be arranged between the electrodes. In various embodiments, the second input may come from an extremity of a user that is on an opposite side of the body than the extremity used for the first input. For example, if the first input is from the left arm, the second input may be from the right arm. As described herein, such cross-body information may be useful for ECG measurements, among other measurements.

In various embodiments, a determination is made that a predetermined time threshold is met (706). This time threshold may correspond to a time for receiving the input data from the first electrode and the second electrode. For example, in determining ECG measurements, a user may need to provide information (e.g., via contact with the electrodes) for a predetermined period of time in order to obtain a satisfactory amount of data. If the time period has been not met, a determination may not be made and the wearable device including the first and second electrodes may provide a notification to the user. However, when the time threshold is satisfied, at least one physical property for the user is determined (708). As an example, the physical property may be an ECG measurement, which evaluates electrical activity of the heart. Additionally, the property may be an EDA measurement. In this manner, a user may utilize a single wearable device, which a comfortable form factor, to provide information for ECG and/or EDA measurements, among other measurements.

Figure 8:
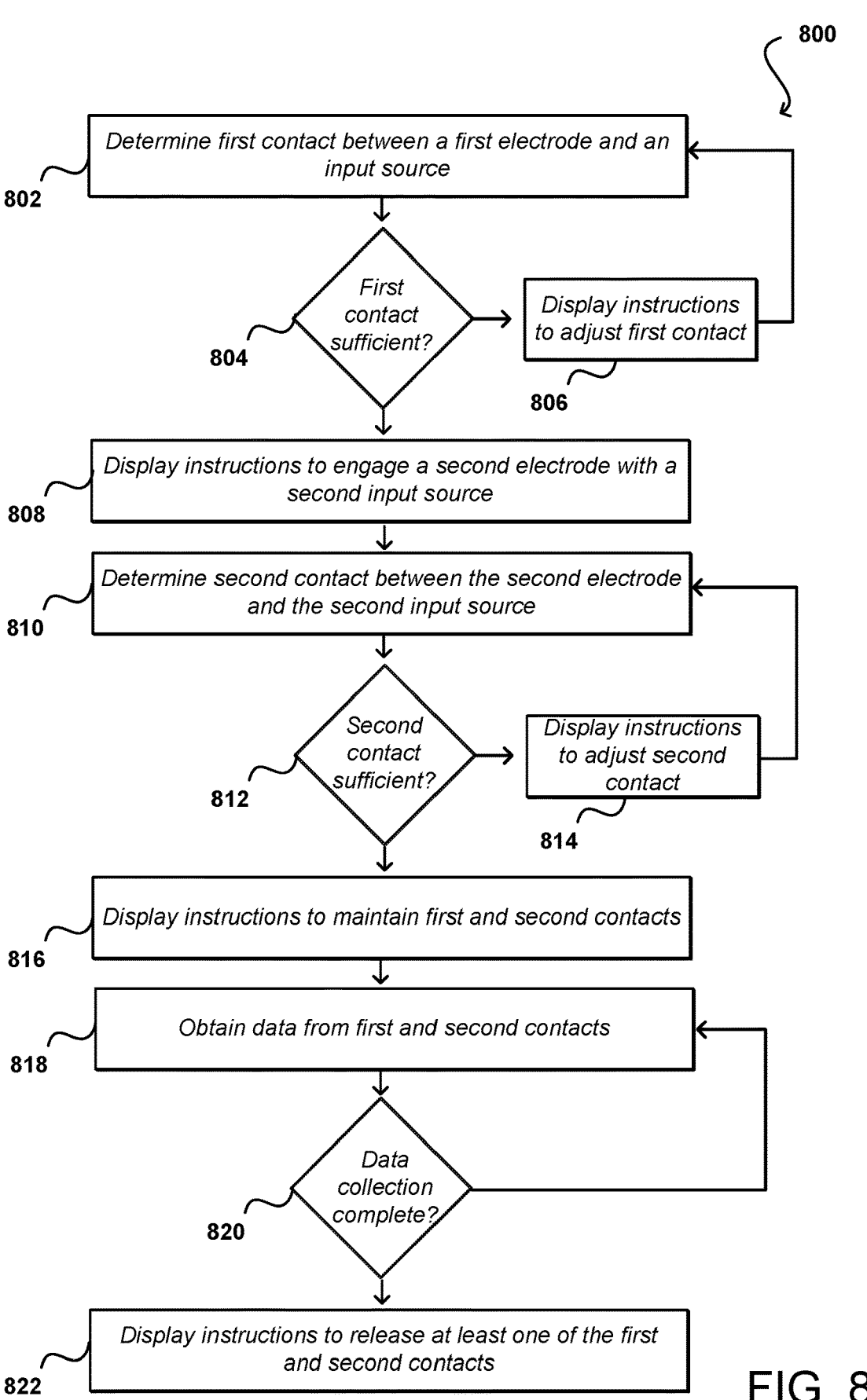
FIG. 8 illustrates an example process for collecting data from a wearable device, in accordance with embodiments of the present disclosure.

FIG. 8 is a flow chart of an example process 800 for obtaining physical measurements from a user of a wearable device. In this example, the wearable device determines a first contact between a first electrode and an input source (802). For example, the first contact may be an extremity of the user, such as a wrist, being in contact with the first electrode. As described, in various embodiments the first contact may be on a lower or bottom side of the wearable device such that wearing the device brings the first electrode into contact with the user. However, it should be appreciated that, in various embodiments, the first contact may be engaged by a leg, a finger, or any other part of the user. The wearable device determines whether the first contact is sufficient (804). For example, movement may interfere with data acquisition, so the user continuously moving may prevent data acquisition. Additionally, there may be interference, such as an article of clothing, that may also hinder data acquisition. If the contact is insufficient, then instructions are displayed to adjust the first contact (806). For example, the display screen 208 may include a message. It should be appreciated that embodiments of the present disclosure are not limiting to displaying the instructions, and instructions may also be conveyed through auditory prompts, through tactile feedback, and the like.

In various embodiments, instructions are further displayed for the user to engage a second electrode with a second input source (808). As noted above, the instructions may be displayed on the display screen 208, and may further include, in addition to or in the alternative, auditory instructions, tactile instructions, and the like. In various embodiments, the instructions may include a graphic to illustrate where the second electrode is, with respect to the wearable device. For example, if the second electrode is along the top surface, the instructions may convey this information (e.g., "Place your hand or wrist across the top face."). Then, the wearable device determines a second contact between the second electrode and the second input source (810). As noted above, the second input source may be an extremity that is different from the extremity used to make the first connection. However, in other embodiments, the second input source may also be the same extremity, for example, when obtaining EDA measurements. The wearable device determines whether the second contact is sufficient (812). If the contact is insufficient, for example due to interference, movement, or the like, then instructions are displayed to adjust the first contact (814). For example, the display screen 208 may include a message, an auditory instruction, a tactile instruction, or a combination thereof.

Once the contacts are established, instructions to maintain the contacts may be displayed (816). As noted above, the instructions may also be accompanied with, or replaced by, auditory instructions, tactile instructions, or the like. For example, if the user is covering the top surface, displaying written instructions on the display screen 208 may not provide information to the user. Accordingly, an auditory instruction may be provided. Moreover, in embodiments, the wearable device may communicate with a consumer device that may receive and display messages to the user. Data may be acquired via the first and second electrodes (818). For example, the data may include EDA measurements, ECG measurements, or any other reasonable measurement data.

For certain types of measurements, data acquisition may have a threshold period of time or a desired period of time. As a result, completion of data collection may be evaluated (820) and may continue if incomplete and display instructions when complete (822). Accordingly, the wearable device may be utilized to acquire data utilizing at least two electrodes that are both incorporated into the wearable device.

Figure 9:
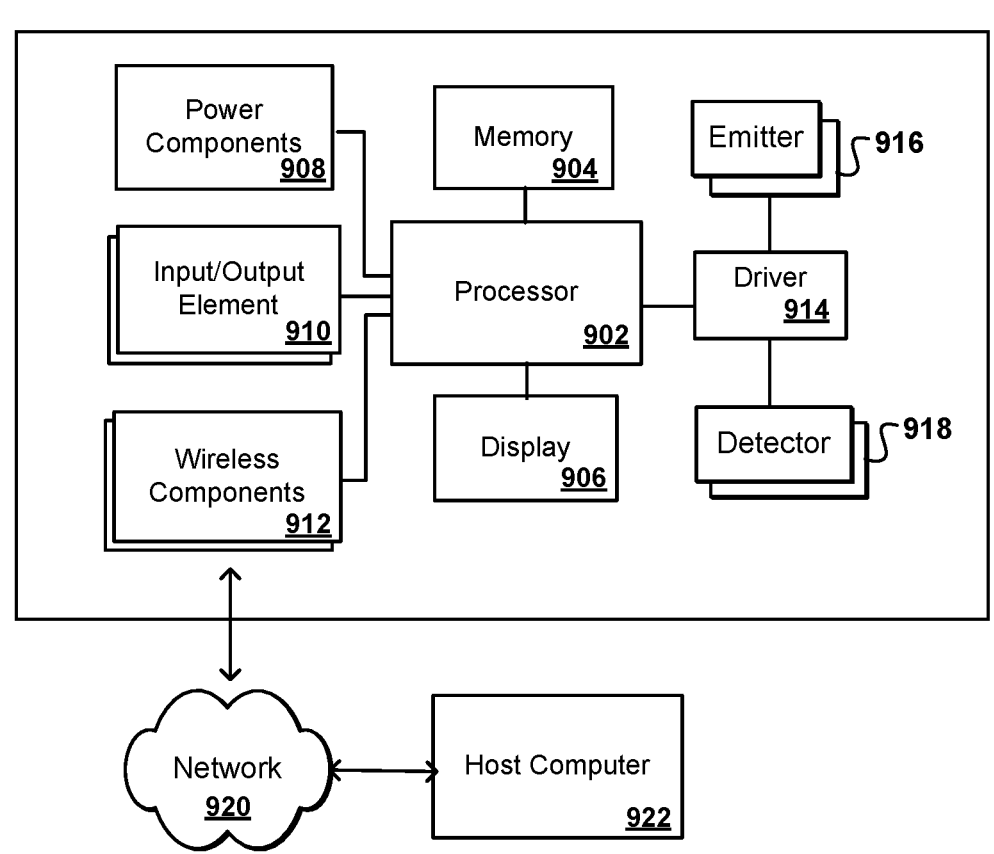
FIG. 9 illustrates a set of basic components of one or more devices of the present disclosure, in accordance with various embodiments of the present disclosure.

FIG. 9 illustrates a set of basic components 900 of one or more devices of the present disclosure, in accordance with various embodiments of the present disclosure. In this example, the device includes at least one processor 902 for executing instructions that can be stored in a memory device or element 904. As would be apparent to one of ordinary skill in the art, the device can include many types of memory, data storage or computer-readable media, such as a first data storage for program instructions for execution by the at least one processor 902, the same or separate storage can be used for images or data, a removable memory can be available for sharing information with other devices, and any number of communication approaches can be available for sharing with other devices. The device may include at least one type of output device 906, such as a touch screen, electronic ink (e-ink), organic light emitting diode (OLED) or liquid crystal display (LCD), although devices such as servers might convey information via other means, such as through a system of lights and data transmissions. The device typically will include one or more networking device 908, such as a port, network interface card, or wireless transceiver that enables communication over at least one network. The device can include at least one input device 910 able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

As discussed, different approaches can be implemented in various environments in accordance with the described embodiments. As will be appreciated, although a Web-based environment is used for purposes of explanation in several examples presented herein, different environments may be used, as appropriate, to implement various embodiments. The system includes an electronic client device, which can include any appropriate device operable to send and receive requests, messages or information over an appropriate network and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server for receiving requests and serving content in response thereto, although for other networks, an alternative device serving a similar purpose could be used, as would be apparent to one of ordinary skill in the art.

The illustrative environment includes at least one application server and a data store. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server can include any appropriate hardware and software for integrating with the data store as needed to execute aspects of one or more applications for the client device and handling a majority of the data access and business logic for an application.

The application server provides access control services in cooperation with the data store and is able to generate content such as text, graphics, audio and/or video to be transferred to the user, which may be served to the user by the Web server in the form of HTML, XML or another appropriate structured language in this example. The handling of all requests and responses, as well as the delivery of content between the client device and the application server, can be handled by the Web server. It should be understood that the Web and application servers are not required and are merely example components, as structured code discussed herein can be executed on any appropriate device or host machine as discussed elsewhere herein. The data store can include several separate data tables, databases or other data storage mechanisms and media for storing data relating to a particular aspect. For example, the data store illustrated includes mechanisms for storing content (e.g., production data) and user information, which can be used to serve content for the production side. The data store is also shown to include a mechanism for storing log or session data. It should be understood that there can be many other aspects that may need to be stored in the data store, such as page image information and access rights information, which can be stored in any of the above listed mechanisms as appropriate or in additional mechanisms in the data store. The data store is operable, through logic associated therewith, to receive instructions from the application server and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a Web page that the user is able to view via a browser on the user device. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated. Thus, the depiction of the systems herein should be taken as being illustrative in nature and not limiting to the scope of the disclosure.

The various embodiments can be further implemented in a wide variety of operating environments, which in some cases can include one or more user computers or computing devices which can be used to operate any of a number of applications. User or client devices can include any of a number of general purpose personal computers, such as desktop or notebook computers running a standard operating system, as well as cellular, wireless and handheld devices running mobile software and capable of supporting a number of networking and messaging protocols. Devices capable of generating events or requests can also include wearable computers (e.g., smart watches or glasses), VR headsets, Internet of Things (IoT) devices, voice command recognition systems, and the like. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wearable computing device, comprising:

a housing including an upper portion and a lower portion, the upper portion and the lower portion being electrically isolated from one another, wherein the lower portion is configured to contact a first body part of a user while the wearable computing device is worn by the user;

a first electrode, provided in the lower portion, the first electrode being positioned to be in contact with the first body part while the wearable computing device is worn by the user;

a second electrode, provided in the upper portion, the second electrode being positioned out of contact from the first body part of the user when the wearable computing device is worn by the user, wherein the second electrode is configured to receive a contact from a second body part of the user;

a third electrode, provided in one of the upper portion and the lower portion, the third electrode being electrically isolated from both the first electrode and the second electrode;

one or more memory devices configured to store instructions; and one or more processors configured to execute the instructions to perform operations, the operations comprising:

determining, based on first data output by the first electrode, a first contact formed between the first body part and the first electrode, determining, based on the first data, whether the first contact formed between the first body part and the first electrode is sufficient based on whether the first contact is maintained more than a first threshold duration of time, when the first threshold duration of time is not satisfied, providing a first output via a user interface instructing the user to adjust at least one of the first body part or the wearable computing device, when the first threshold duration of time is satisfied, providing a second output via the user interface instructing the user to bring the second body part into contact with the second electrode, determining, based on second data output by the second electrode, a second contact formed between the second body part and the second electrode, determining, based on the second data, whether the second contact formed between the second body part and the second electrode is sufficient based on whether the second contact is maintained more than a second threshold duration of time, when the second threshold duration of time is not satisfied, providing a third output via the user interface instructing the user to adjust at least one of the second body part or the wearable computing device, when the second threshold duration of time is satisfied, providing a fourth output via the user interface instructing the user to maintain the first contact and the second contact, acquiring, while the first contact and the second contact are maintained, the first data via the first electrode and the second data acquired via the second electrode, when the first data and the second data are acquired while the first contact and the second contact are maintained for less than a third threshold duration of time, determining collection of the first data and the second data is incomplete, and when the first data and the second data are acquired while the first contact and the second contact are maintained for more than the third threshold duration of time, evaluating the first data and the second data and outputting a biometric measurement based on the first data and the second data acquired while the first contact and the second contact were maintained for more than a third threshold duration of time.

2. The wearable computing device of claim 1, wherein the upper portion comprises:

a display screen configured to provide at least one of the first output or the second output; and a bezel, wherein the bezel substantially surrounds a perimeter of the display screen, the bezel being electrically isolated from the display screen and the lower portion.

3. The wearable computing device of claim 2, wherein the second electrode and the third electrode are formed on the display screen, the display screen being visible through the second electrode and the third electrode.

4. The wearable computing device of claim 2, wherein the upper portion comprises:

a bezel extending around a perimeter of the upper portion, wherein both the second electrode and the third electrode are arranged within the bezel.

5. The wearable computing device of claim 1, wherein the upper portion includes a display screen configured to provide at least one of the first output or the second output, and the housing further includes a conductive ring disposed around the display screen, and the conductive ring includes the second electrode and the third electrode.

6. The wearable computing device of claim 1, further comprising at least one spacer positioned between each of the first electrode, the second electrode, and the third electrode, the spacer electrically isolating the first electrode, the second electrode, and the third electrode from one another.

7. The wearable computing device of claim 1, wherein the one or more processors are configured to provide at least one of the first output or the third output via the user interface via at least one of a textual message, an auditory sound, or tactile feedback.

8. The wearable computing device of claim 1, wherein the biometric measurement includes at least one of an electrocardiogram measurement or an electrodermal activity measurement.

9. A method for obtaining a biometric measurement via a plurality of electrodes provided in a housing of a wearable computing device, the method comprising:

determining, based on first data output by a first electrode among the plurality of electrodes, a first contact formed between a first body part of a user and the first electrode, wherein the first electrode is provided in a lower portion of the housing and is positioned to be in contact with the first body part while the wearable computing device is worn by the user;

determining, based on the first data, whether the first contact formed between the first body part and the first electrode is sufficient based on whether the first contact is maintained more than a first threshold duration of time;

when the first threshold duration of time is not satisfied, providing a first output via a user interface instructing the user to adjust at least one of the first body part or the wearable computing device;

when the first threshold duration of time is satisfied, providing a second output via a user interface instructing the user to bring a second body part of the user into contact with a second electrode among the plurality of electrodes;

determining, based on second data output by the second electrode, a second contact formed between the second body part and the second electrode, wherein the second electrode is provided in an upper portion of the housing and is positioned out of contact from the first body part of the user when the wearable computing device is worn by the user, wherein the second electrode is configured to receive a contact from the second body part of the user and the upper portion and the lower portion of the housing are electrically isolated from one another;

determining, based on the second data, whether the second contact formed between the second body part and the second electrode is sufficient based on whether the second contact is maintained more than a second threshold duration of time, when the second threshold duration of time is not satisfied, providing a third output via the user interface instructing the user to adjust at least one of the second body part or the wearable computing device, when the second threshold duration of time is satisfied, providing a fourth output via the user interface instructing the user to maintain the first contact and the second contact, acquiring, while the first contact and the second contact are maintained, the first data via the first electrode and the second data via the second electrode, when the first data and the second data are acquired while the first contact and the second contact are maintained for less than a third threshold duration of time, determining collection of the first data and the second data is incomplete, and when the first data and the second data are acquired while the first contact and the second contact are maintained for more than the third threshold duration of time, evaluating the first data and the second data and outputting a biometric measurement based on the first data and the second data acquired while the first contact and the second contact were maintained for more than a third threshold duration of time.

10. The method of claim 9, wherein the first body part includes a wrist of a first limb and the second body part includes a second limb.

11. The method of claim 9, comprising:

determining, based on third data output by a third electrode among the plurality of electrodes, a third contact formed between a third body part of the user and the third electrode, wherein the third electrode is provided in the upper portion of the housing and is positioned out of contact from the third body part of the user when the wearable computing device is worn by the user;

determining, based on the third data, whether the third contact formed between the third body part and the third electrode satisfies a fourth threshold duration of time;

when the fourth threshold duration of time is not satisfied, providing a fifth output via the user interface instructing the user to adjust at least one of the third body part or the wearable computing device;

when the fourth threshold duration of time is satisfied, providing a sixth output via the user interface instructing the user to bring the second body part of the user into contact with the second electrode;

determining, based on fourth data output by the second electrode, the second contact formed between the second body part and the second electrode while the third contact is maintained between the third body part and the third electrode; and obtaining, while the third contact and the fourth contact are maintained, another biometric measurement based on the fourth data acquired via the second electrode and the third data acquired via the third electrode.

12. The method of claim 11, wherein the second body part includes a first finger on a first limb and the third body part includes a second finger on a second limb.

13. The method of claim 11, further comprising providing at least one spacer between each of the first electrode, the second electrode, and the third electrode, the spacer electrically isolating the first electrode, the second electrode, and the third electrode from one another.

14. The method of claim 11, further comprising providing the second electrode and the third electrode in a display screen of the wearable computing device.

15. A non-transitory computer readable medium storing instructions which, when executed by a processor, cause the processor to perform operations for obtaining a biometric measurement via a plurality of electrodes provided in a housing of a wearable computing device, the operations comprising:

determining, based on first data output by a first electrode among the plurality of electrodes, a first contact formed between a first body part of a user and the first electrode, wherein the first electrode is provided in a lower portion of the housing and is positioned to be in contact with the first body part while the wearable computing device is worn by the user;

determining, based on the first data, whether the first contact formed between the first body part and the first electrode is sufficient based on whether the first contact is maintained more than a first threshold duration of time;

when the first threshold duration of time is not satisfied, providing a first output via a user interface instructing the user to adjust at least one of the first body part or the wearable computing device;

when the first threshold duration of time is satisfied, providing a second output via the user interface instructing the user to bring a second body part of the user into contact with a second electrode among the plurality of electrodes;

determining, based on second data output by the second electrode, a second contact formed between the second body part and the second electrode, wherein the second electrode is provided in an upper portion of the housing and is positioned out of contact from the first body part of the user when the wearable computing device is worn by the user, wherein the second electrode is configured to receive a contact from the second body part of the user and the upper portion and the lower portion of the housing are electrically isolated from one another;

determining, based on the second data, whether the second contact formed between the second body part and the second electrode is sufficient based on whether the second contact is maintained more than a second threshold duration of time;

when the second threshold duration of time is not satisfied, providing a third output via the user interface instructing the user to adjust at least one of the second body part or the wearable computing device;

when the second threshold duration of time is satisfied, providing a fourth output via the user interface instructing the user to maintain the first contact and the second contact;

acquiring, while the first contact and the second contact are maintained, the first data via the first electrode and the second data via the second electrode;

when the first data and the second data are acquired while the first contact and the second contact are maintained for less than a third threshold duration of time, determining collection of the first data and the second data is incomplete, and when the first data and the second data are acquired while the first contact and the second contact are maintained for more than the third threshold duration of time, evaluating the first data and the second data and outputting a biometric measurement based on the first data and the second data acquired while the first contact and the second contact were maintained for more than a third threshold duration of time.

* * * * *